United States Patent [19]
Kovacic

[11] 3,977,393
[45] Aug. 31, 1976

[54] PRESSURE CUFF AND METHOD OF PLACING IT ON A LIMB

[76] Inventor: Victor E. Kovacic, 33076 Lakeshore Blvd., Eastlake, Ohio 44094

[22] Filed: Dec. 18, 1974

[21] Appl. No.: 532,891

[52] U.S. Cl. .................. 128/2.05 C; 128/2.05 G; 128/327; 128/DIG. 15
[51] Int. Cl.² ......................................... A61B 5/02
[58] Field of Search ............... 128/2.05 C, 2.05 A, 128/2.05 G, 2.05 M, 2.05 R, 327, DIG. 15; 2/170, DIG. 6; 24/DIG. 18

[56] References Cited
UNITED STATES PATENTS

| | | | |
|---|---|---|---|
| 1,063,287 | 6/1913 | Rogers et al. | 128/2.05 G |
| 3,000,384 | 9/1961 | Piers | 128/DIG. 15 |
| 3,633,567 | 1/1972 | Sarnoff | 128/2.05 C |
| 3,827,107 | 8/1974 | Moore | 128/DIG. 15 |
| 3,857,397 | 12/1974 | Brosseau | 128/384 |

*Primary Examiner*—Robert W. Michell
*Assistant Examiner*—Lee S. Cohen

[57] ABSTRACT

A pneumatic cuff or sleeve for detecting blood pressure in a limb of a body is provided with a locking assembly which allows the cuff to be easily affixed around the limb without shifting the cuff thereon. The locking assembly utilizes a tab member, formed at one end of the cuff, and an aperture formed at the other end of the cuff. The aperture is slightly spaced from the opposite end of the cuff to allow the opposite end to be grasped. In use, the cuff is placed around the limb in the proper measuring area and tab member is threaded through the aperture. The threaded tab member and the opposite end of the cuff are pulled in opposite directions to tighten the cuff without circumferentially shifting the cuff from the measuring area. The tab and the opposite end of the cuff have pressure sensitive material thereon which mates with the outside of the cuff to retain the tab and the end of the cuff thereby retaining the cuff around the limb.

6 Claims, 4 Drawing Figures

PRESSURE CUFF AND METHOD OF PLACING IT ON A LIMB

BACKGROUND OF THE INVENTION

1. Field of the Invention

The present invention relates to sphygmomanometers or blood pressure measuring devices generally and particularly to sphygmomanometers having a locking mechanism which allows the cuff to be easily affixed around the limb of a body without shifting it thereon.

2. Description of the Prior Art

In the measurement of blood pressure, a sphygmomanometer assembly includes a cuff which is wrapped around the limb to thereby measure blood pressure. The cuff has a measuring area which must be accurately placed against the veins of the limb to produce an accurate measurement.

Known prior art cuffs were applied to the limb by placing one end of the cuff on the limb and then wrapping the other end around the limb to capture the first end. Difficulties occur in such a placement since the cuff tends to circumferentially shift around the limb due to the pulling action on the single opposite cuff end. When the cuff shifts, an inaccurate measurement occurs. An example of such prior art cuffs may be found in U.S. Pat. No. 3,765,405 issued to F. Natkanski.

Since the end of the cuff which is placed initially on the limb must be manually retained before it is captured by overlapping it with the opposite end, some bandages or cuffs utilize mechanical locking assemblies. In such assemblies a slotted buckle is affixed to one end of the cuff and the opposite end is threaded therethrough. The cuff is then tightened by pulling on the threaded end. An example of such locking assemblies may be found in U.S. Pat. Nos. 3,713,446 and 3,633,567 issued to S. J. Sarnoff. However, since the cuff is pulled at a single end the tendency to circumferentially move the cuff is still present and inaccurate measurements still occur. Such locking assemblies are also costly to manufacture and tend to break easily.

SUMMARY OF THE INVENTION

The present invention solves the problems associated with the prior art devices as well as other problems by providing a unique cuff which is easily and accurately placed around the limb without causing a circumferential shift in the cuff. To accomplish the above the cuff is formed as a flat elongated body member having a tab formed at one end and having an aperture formed at the opposite end. The tab is threaded through the aperture and both the tab and the aperture end of the cuff are pulled in opposite directions to tighten the cuff around the limb. The cuff has locking means to retain the ends of the cuff in the tightened position.

The aperture is formed as a rectangular elongated slot to provide an adjustable enclosure for various size limbs. The slot is spaced from an end of the cuff to provide a grasping area to tighten the cuff by pulling the grasping area and the tab in opposite directions. The outside of the cuff, as well as the grasping area and the tab, have pressure sensitive material thereon to allow the cuff to be retained around the limb by locking the tab and the grasping area to the outside of the cuff.

In view of the foregoing, it will be seen that one aspect of the present invention is to provide a cuff that is easily placed around a limb without circumferentially shifting the cuff.

Another aspect of the present invention is to provide a cuff that is tightened on a limb by pulling opposite ends of the cuff in opposite directions.

These and other aspects of the present invention will be more readily understood after a review of the following description of the preferred embodiment considered with the drawings.

DESCRIPTION OF THE PREFERRED EMBODIMENT

Figure 1:
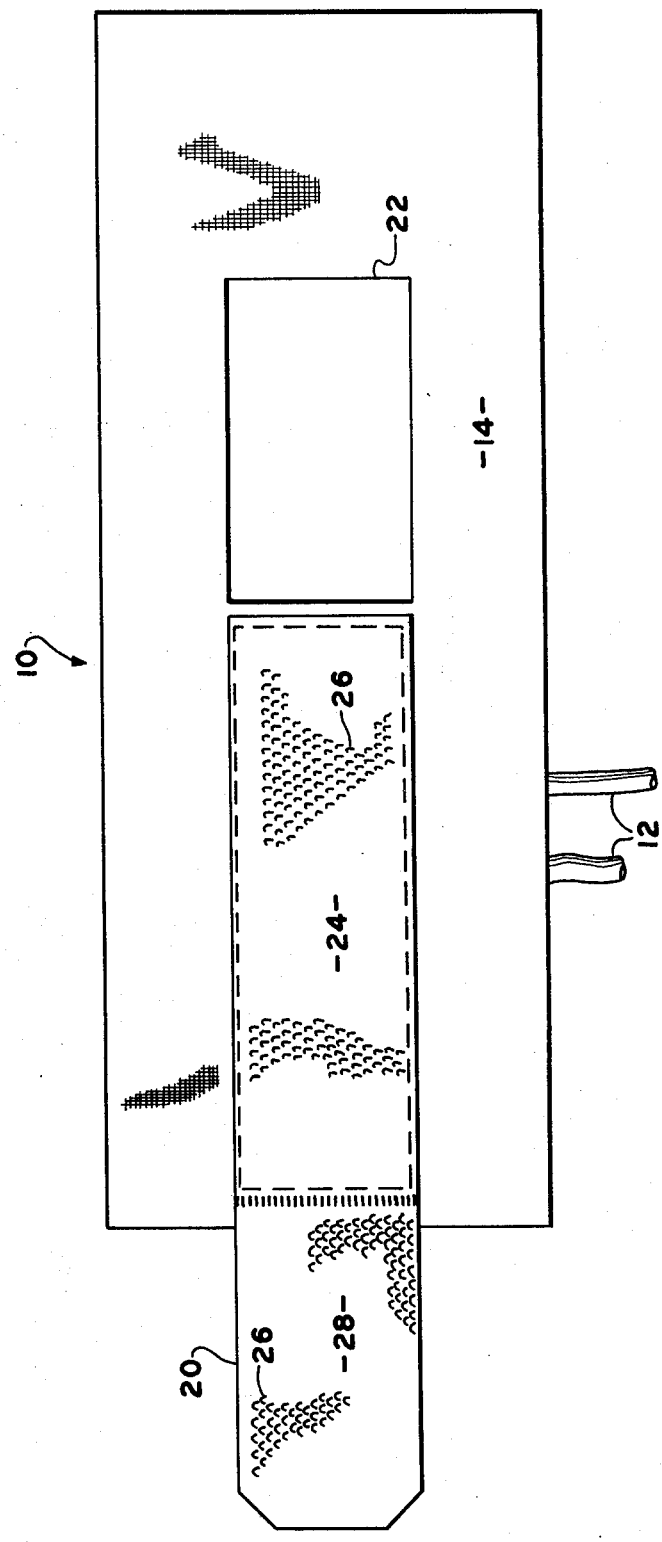
FIG. 1 depicts the cuff of the present invention longitudinally extended with the non-measuring side up.

Referring now to the drawing, it will be understood that the showings therein are intended to describe a preferred embodiment of the present invention but that the invention is not limited thereto.

Figure 2:
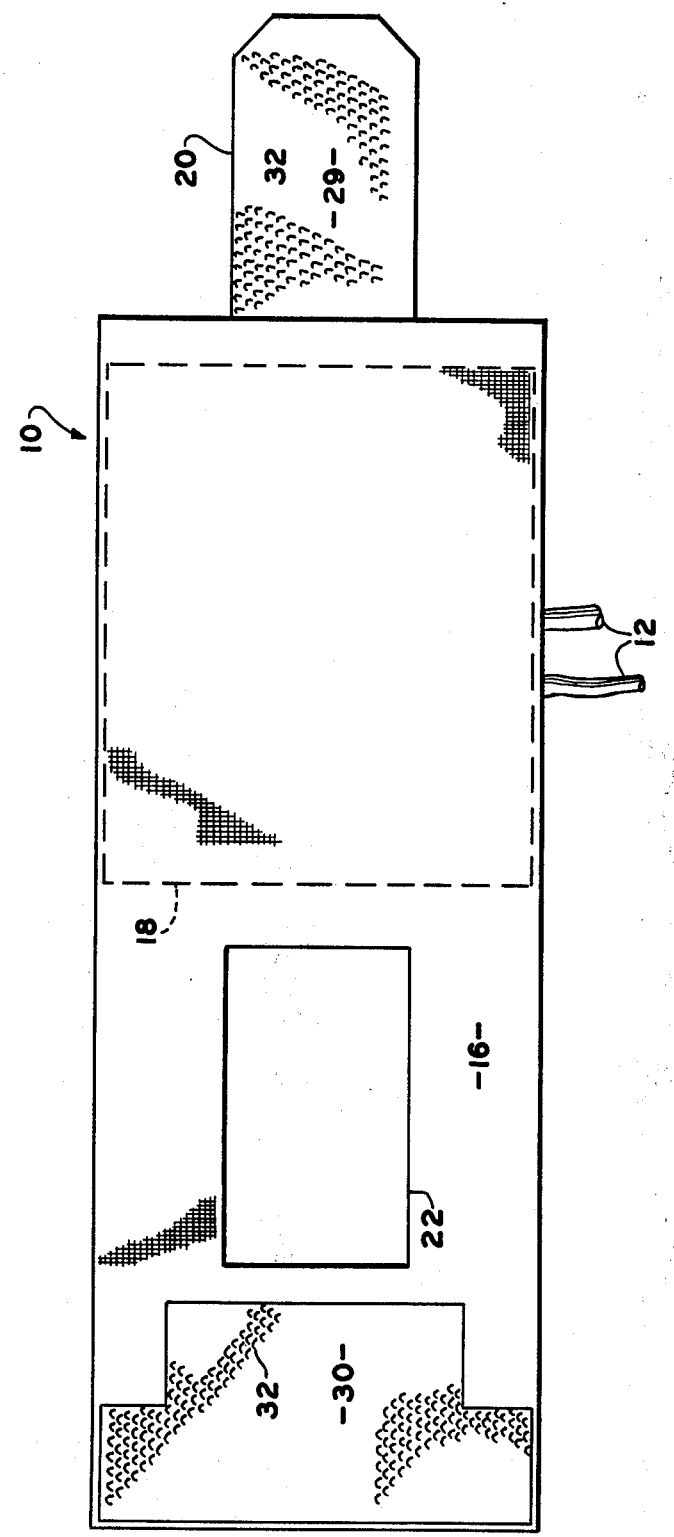
FIG. 2 depicts the measuring side of the cuff of FIG. 1.

Turning now to FIGS. 1 and 2, a cuff member 10 is shown to have an elongated body portion within which a well known bladder is enclosed (not shown) connected by lines 12 to a blood pressure measuring assembly (not shown). The cuff 10 has an outside surface 14 and an inside surface 16 on which a measuring area 18 is located. The measuring area 18 is placed against a blood vessel of a limb and the cuff 10 is wrapped around the limb to retain it there. The bladder is then pressurized through one of the lines 12 and the back pressure provided by the blood flowing in the vein is detected by the pressure measuring assembly (not shown) which is connected to the cuff 10 through the other of the lines 12.

The cuff 10 is made to have a tab member 20 attached at one end and a rectangular slot 22 cut out near the other end. The slot 22 is sized to be larger than the tab member 20 to allow the tab member to be threaded through the slot 22. The slot is also elongated to allow the cuff to be adjustable to fit limbs of various diameters. The outside surface 14 of the cuff 10 has a "Velcro" patch 24 comprised of a series of loops 26 which are matable with a mating surface to be described later. The tab member 20 also has a "Velcro" patch comprised of the same loops 26 as the patch 24. The inside surface 16 of the cuff 10 has a mating Velcro patch 30 comprised of a series of bristles 32 which intertwine with the loops 26 to bind their respective surfaces whenever the bristles 32 are pressed together with the loops 26.

Figure 3:
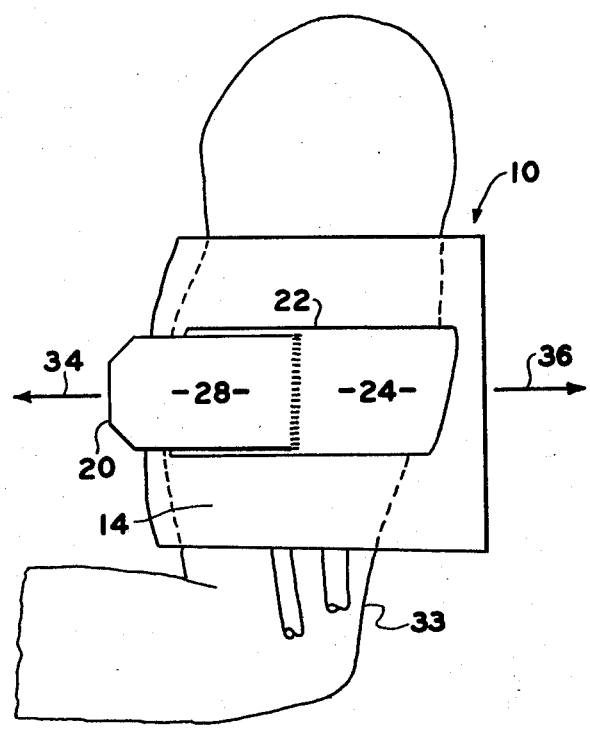
FIG. 3 depicts the cuff of the present invention being placed on an arm to measure blood pressure.
Figure 3A:
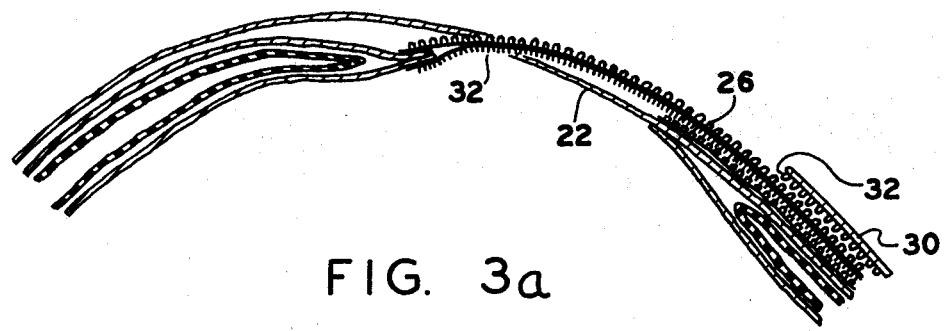
FIG. 3a is an expanded top view of the locking area of the cuff of FIG. 3.

Referring now to FIGS. 3 and 3a, it will be seen that the measuring area 18 of cuff 10 is placed against a vein of an arm 33 and the tab member 20 is threaded through the slot 22. The cuff 10 is tightened by pulling the tab member 20 in a first direction indicated by an arrow 34 and by pulling the slot 22 end of the cuff 10 in a second direction indicated by an arrow 36. The cuff is thereby tightened around the arm 33 without shifting the measuring area 18 of the cuff 10 circumferentially around the arm 33. As best seen in FIG. 3a, the bristles 32 on the opposite tab surface 29 of the tab 20 are pressed into engagement with the loop 26 on the patch 24 to lock the tab 20 to the outside surface 14 of the cuff 10. The other end of the cuff 10 is wrapped around the arm and the patch 30 is similarly locked to the patch 24 by pressing the bristles 32 of the patch 30 into the loops 26 of the patch 24. In cases of very small limbs, the slot 22 end of the cuff 10 will overlap the tab member 20. However, locking will still occur between the tab 20 and the patch 30 since the bristles 32 of the patch 30 will be pressed into the loops 26 on the surface of the tab 20.

Certain modifications and improvements will occur to those skilled in the art upon the reviewing the foregoing specification. It will be understood that such modifications and improvements have been deleted for the sake of conciseness and readability but that they are included within the scope of the claims.

I claim:

1. A sphygmomanometer cuff having a bladder inflatable by inflating means and being adapted to be positioned around the limb of a body by pulling on opposite sides of the cuff comprising:
    inflating means;
    a flexible band-type member having a rectangular body with a bladder connected to said inflating means located on one surface therealong, said band-type member being adapted to be wrapped around the limb with the bladder located in the area of a vein of the limb;
    a tab member formed at one end of the band-type member;
    said band-type member having an aperture formed at the end of the rectangular body opposite said tab member, said aperture being spaced from said opposite end of the band-type member to leave an end grasping area between the aperture and said end, said tab member being of a size to allow its threading through the aperture to allow said band-type member to be tightly positioned around the limb without being circumferentially shifted thereon by pulling said threaded tab member in one direction and the end grasping area of said opposite end of said band-type member in a second direction opposite said first direction to tighten said cuff around the limb without shifting the bladder from the vein of the limb;
    first locking means located on a surface of said band-type member opposite the bladder area;
    second locking means located on said tab on the same surface as said bladder; and
    a third locking means located on said grasping area on the same surface as said bladder, said second locking means of said tab and said third locking means of said end grasping area of the band-type member being of a type which is individually lockable to said first locking means to retain the cuff tightly on the limb and prevent circumferential shifting thereon.

2. A cuff as set forth in claim 1 wherein the aperture is formed as an elongated rectangle to allow said band-type member to adjustably encompass limbs of different sizes.

3. A cuff as set forth in claim 2 wherein said second locking means of said tab member is formed from pressure sensitive material and (the outside of said band-type member has formed thereon) and said first locking means includes an extended strip of pressure sensitive material of a type matable with said second locking means of said tab member to allow said tab member to be retained in various positions (thereby having said band-type member encompass various size limbs).

4. A cuff as set forth in claim 3 wherein the third locking means (end grasping area of said band-like member proximate to the aperture) includes pressure sensitive material of a type which is also matable with said extended strip of pressure sensitive material (on the outside of said band-like member).

5. A method of placing a sphygmomanometer cuff on a limb without circumferentially shifting it thereon comprising the steps of:
    providing a cuff having a pressure sensing area on one side and a first locking means on the opposite side, said cuff also having a tab at one end having on said one side second locking means of a type matable with said first locking means and an aperture at the opposite end but spaced therefrom to leave an end grasping area having on said one side third locking means of a type matable with said first locking means;
    placing the cuff on the limb to align the pressure sensing area of the cuff with a vein of the limb;
    threading the tab through the aperture;
    pulling the tab and the grasping area in opposite directions to allow tightening of the cuff around the limb without circumferentially moving the pressure sensing area of the cuff from the vein, and
    individually engaging the second matable locking means and the third matable locking means with the first locking means to retain opposite direction tension on the tab and the grasping end to thereby retain the tightened cuff on the limb.

6. A method as set forth in claim 5 wherein said step of individually engaging includes the steps of:
    engaging the second locking means with said first locking means;
    engaging the third locking means with said first locking means.

* * * * *